United States Patent [19]

Goward

[11] Patent Number: 5,310,670

[45] Date of Patent: May 10, 1994

[54] METHOD FOR THE PURIFICATION OF ERWINIA L-ASPARAGINASE

[75] Inventor: Christopher R. Goward, London, England

[73] Assignee: Public Health Laboratory Service Board, London, England

[21] Appl. No.: 867,105

[22] PCT Filed: Aug. 1, 1991

[86] PCT No.: PCT/GB91/01308

§ 371 Date: Jun. 25, 1992

§ 102(e) Date: Jun. 25, 1992

[87] PCT Pub. No.: WO92/02616

PCT Pub. Date: Feb. 20, 1992

[30] Foreign Application Priority Data

Aug. 2, 1990 [GB] United Kingdom ............... 9017002

[51] Int. Cl.$^5$ .................................... C12N 9/82
[52] U.S. Cl. ................... 435/229; 435/815; 435/847
[58] Field of Search .............. 435/229, 815, 847

[56] References Cited

U.S. PATENT DOCUMENTS

| | | | |
|---|---|---|---|
| 3,594,282 | 7/1971 | Kawaga et al. | 435/229 |
| 3,597,323 | 8/1971 | Roberts | 435/229 |
| 3,637,462 | 1/1972 | Hill et al. | 435/229 |
| 4,729,957 | 3/1988 | Lee et al. | 435/229 |

FOREIGN PATENT DOCUMENTS

| | | | |
|---|---|---|---|
| 0436085 | 7/1974 | U.S.S.R. | 435/229 |
| 1208225 | 10/1970 | United Kingdom | 435/229 |

*Primary Examiner*—Herbert J. Lilling
*Attorney, Agent, or Firm*—Kirschstein, Ottinger, Israel & Schiffmiller

[57] ABSTRACT

A process is provided for the purification of L-asparaginase by contacting a crude extract of L-asparaginase with a solid medium having cation exchange groups so as to adsorb L-asparaginase on the support and eluting adsorbed L-asparaginase from the support. The cation exchange groups comprise sulphonate groups and the elution step is carried out at a pH which is higher than the pH used in the contacting step.

10 Claims, 2 Drawing Sheets

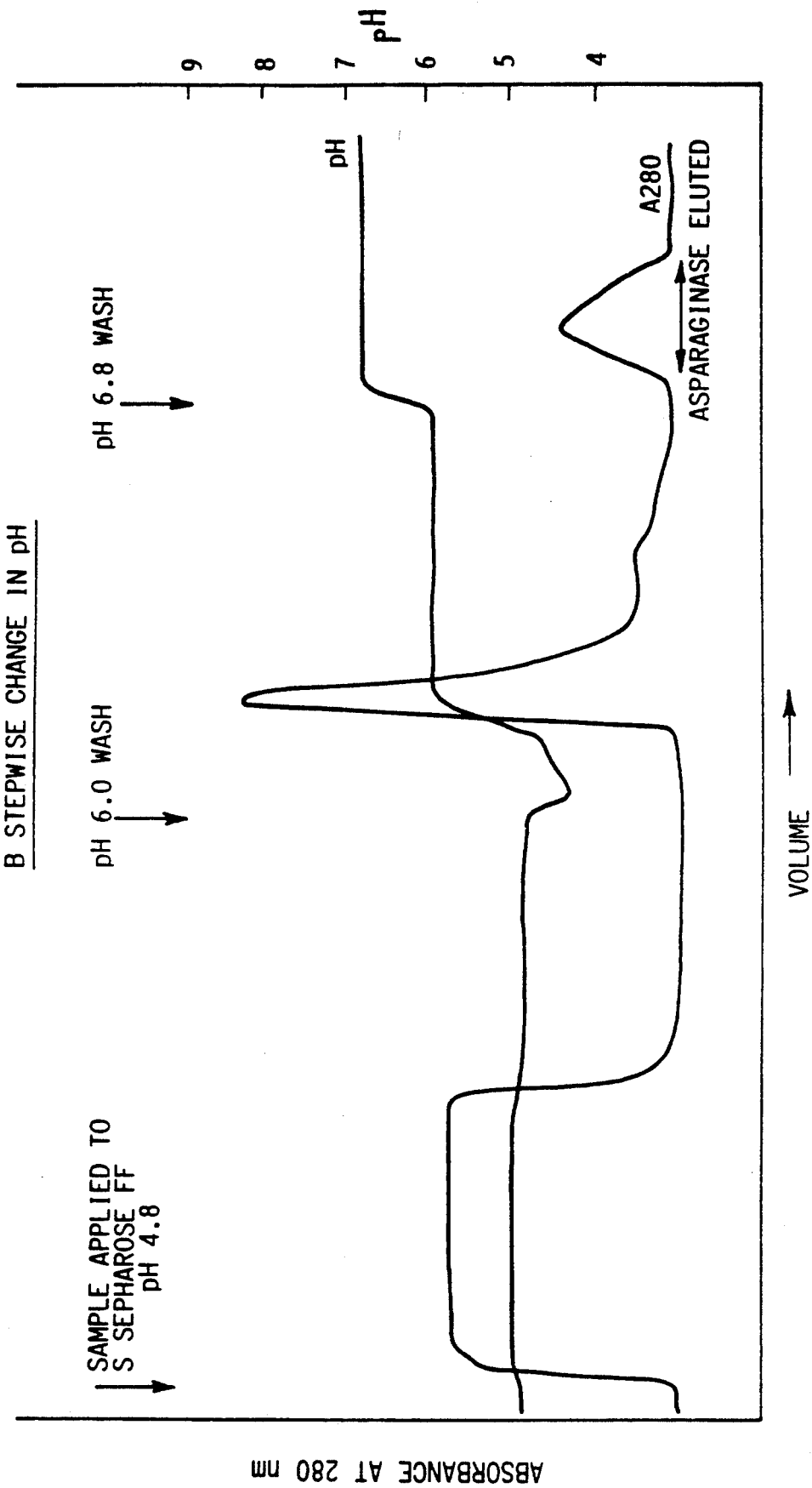

SEQUENCE LISTING ( 1 ) GENERAL INFORMATION:

( i i i ) NUMBER OF SEQUENCES: 1

( 2 ) INFORMATION FOR SEQ ID NO: 1:

( i ) SEQUENCE CHARACTERISTICS:
  ( A ) LENGTH: 327 a.a.
  ( B ) TYPE: Amino acid
  ( C ) STRANDEDNESS:
  ( D ) TOPOLOGY: Linear ( i i ) MOLECULE TYPE: Polypeptide
  ( A ) DESCRIPTION: The amino acid sequence of Erwinia chrysanthemi L-asparaginase ( i i i ) HYPOTHETICAL: No ( v i ) ORIGINAL SOURCE:
  ( A ) ORGANISM: Erwinia chrysanthemi ( x i ) SEQUENCE DESCRIPTION: SEQ ID NO: 1:

```
Ala  Asp  Lys  Leu  Pro  Asn  Ile  Val  Ile  Leu  Ala  Thr  Gly  Gly  Thr  Ile
 1              5                        10                       15

Ala  Gly  Ser  Ala  Ala  Thr  Gly  Thr  Gln  Thr  Thr  Gly  Tyr  Lys  Ala  Gly
```

-continued

```
                    20                      25                      30
Ala Leu Gly Val Asp Thr Leu Ile Asn Ala Val Pro Glu Val Lys Lys
            35                      40                      45
Ser Glu Asn Leu Ala Asn Val Lys Gly Glu Gln Phe Ser Asn Met Ala
                    50                      55                      60
Asn Glu Leu Met Thr Gly Asp Val Val Leu Lys Leu Ser Gln Arg Val
                    65                      70                      75
        80
Gly Thr Asp Leu Ala Arg Asp Asp Val Asp Gly Val Val Ile Thr His
                            85                      90
        95
Thr Val Glu Glu Ser Ala Tyr Phe Leu His Leu Thr Val Lys Ser Asp
                100                     105                     110
Lys Pro Val Val Phe Val Ala Ala Met Arg Pro Ala Thr Ala Ile Ser
                115                     120                     125
Ala Asp Gly Pro Met Asn Leu Leu Glu Ala Val Arg Val Ala Gly Asp
                    130                     135                     140
Lys Gln Ser Arg Gly Arg Gly Val Met Val Val Leu Asn Asp Arg Ile
145                     150                     155                     160
Leu Asp Thr Gly Ser Ala Arg Tyr Ile Thr Lys Thr Asn Ala Ser Thr
                        165                     170
        175
Gly Asn Arg Phe Lys Ala Asn Glu Glu Gly Tyr Leu Gly Val Ile Ile
                        180                     185
190
Arg Ser Val Ile Tyr Tyr Gln Asn Arg Ile Asp Lys Leu His Thr Thr
                        195                     200                     205
Asp Ile Leu Tyr Phe Asp Val Arg Gly Leu Thr Ser Leu Pro Lys Val
                        210                     215                     220
Gln His Gly Tyr Gln Asp Asp Pro Glu Tyr Leu Tyr Asp Ala Ala Ile
                        225                     230                     235
        240
Val Ser Gly Val Lys Gly Ile Val Tyr Ala Gly Met Gly Ala Gly Ser
                        245                     250
255
Val Val Val Arg Gly Ile Ala Gly Met Arg Lys Ala Met Glu Lys Gly
                        260                     265                     270
Asp Glu Val Ile Arg Ser Thr Arg Thr Gly Asn Gly Ile Val Pro Pro
                        275                     280                     285
Ala Arg Glu Leu Pro Gly Leu Val Ser Asp Ser Leu Asn Pro Ala His
                        290                     295                     300
Val Ile Ile Leu Leu Met Leu Ala Leu Thr Arg Thr Ser Asp Pro Lys
                        305                     310                     315
        320
```

```
Gln Glu Tyr Phe His Thr Tyr
          325
```

METHOD FOR THE PURIFICATION OF ERWINIA L-ASPARAGINASE

This invention relates to a process for the purification of L-asparaginase.

L-asparaginase has been reported to occur in a range of bacteria, fungi, plants and mammals and its presence in Gram-negative bacteria has been well documented (Wriston & Yellin, 1973; Wriston, 1985). L-asparaginases have considerable commercial importance because some of these enzymes particularly those from *Escherichia coli* (asparaginase II) and *Erwinia chrysanthemi* are effective against acute lymphoblastic leukaemia (Wriston, 1985). The enzymes from Erwinia and *E. coli* show no immunological cross-reactivity and so can provide an alternative therapy for a patient who has become hypersensitive to one of these enzymes. (Cammack et al., 1982). The enzyme from Erwinia is a tetramer of relative molecular mass 140,000, with four identical subunits, and has an unusually high isoelectric point of pH 8.6.

Hitherto, L-asparaginases have been prepared on a large scale by a combination of batch and column ion-exchange chromatography. A large number of stages are required to attain the necessary purity, with batch ion-exchange chromatography being particularly labour-intensive. Current commercial practice involves the growth of a cell culture, and then a crude protein extraction employing alkali disruption and acid precipitation. The resulting extract is then subjected to adsorption to and elution from CM-cellulose. There then follows a further acid precipitation step and chromatography steps using CM and DEAE-cellulose media. One of the major problems of the system is its complexity, thus it is not readily automated and cannot be easily adapted for continuous operation.

We have now developed a new method of L-asparaginase purification resulting in a product of astonishing quality with a simplified process and the advantage of allowing for increased automation.

According to the present invention there is provided a process for producing purified L-asparaginase which comprises (a) contacting a crude extract of L-asparaginase with a solid medium having cation exchange groups so as to adsorb L-asparaginase on the support and (b) eluting adsorbed L-asparaginase from the support, characterised in that the cation exchange groups comprise sulphonate groups and the elution step (b) is carried out at a pH which is higher than the pH used in step (a) and preferably is less than 8.0.

The cation sulphonate ($-SO_3^-$), groups may be provided, for example, by groups of the formula

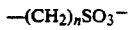

wherein n is equal to 1 to 3.

The nature of the matrix of the solid medium is not unduly critical, but in order to achieve a high flow rate in a continuous process a support with a high degree of porosity is preferred. Other desirable characteristics include rigidity, low non-specific binding of protein and general chemical stability. It has been found that these properties are provided by agarose or an agarose derivative.

In carrying out the process of the invention, crude dilute extract of L-asparaginase is preferably applied to the solid medium at a pH of from 4.0 to 5.5, followed by a washing step of pH 6.0. Elution of adsorbed L-asparaginase may then be effected with a suitable buffer solution of pH in the range 6.0 to 7.5. This range is preferably between 6.5 to 7.0.

The process of the invention may be advantageous applied to the purification of the L-asparaginase of *E chrysanthemi*. Although as mentioned above, L-asparaginases are fairly ubiquitous in prokaryotes and eukaryotes alike, that of *E chrysanthemi* is preferably used for this process because of its therapeutic utility. Thus the process of the invention may be employed to purify L-asparaginases extracted form cultures of *E chrysanthemi* or it may be employed to purify L-asparaginase from other sources. Examples include L-asparaginase having amino acid sequences related to that of the Erwinia enzyme. In order to retain a reasonably high specific activity it is desirable to retain a close sequence homology (e.g. >90%, most preferably >95%) with the wild type. The amino acid sequence of the wild type protein is see forth below.

This process may also be used for purification of L-asparaginase obtained from organisms subjected to transformation or other cloning techniques whereby the *E chrysanthemi* L-asparaginase gene is linked to systems promoting super-expression.

BRIEF DESCRIPTION OF THE DRAWINGS

FIG. 2 is an elution profile as in FIG. 1 but with the pH of the wash solution increased in stepwise fashion from 4.8 to 6.0 to 6.8.

Figure 1:
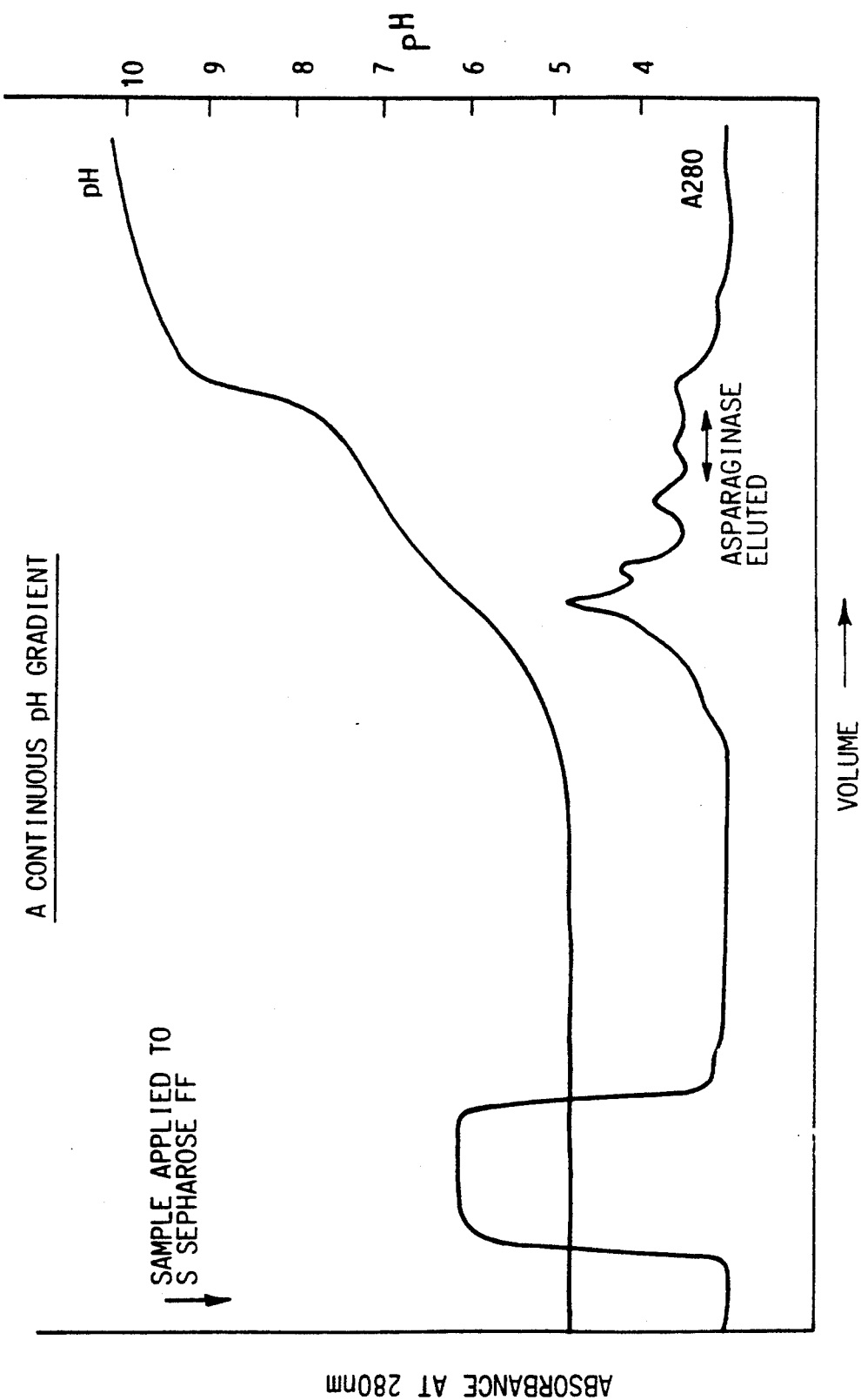
FIG. 1 is an elution profile of absorbance of protein monitored on an optical spectrometer at 280 nm of an extract of *E. chrysanthemi* prepared in accordance with Example 1 and eluted from a column of S-Sepharose Fast Flow, with the pH of the wash solution increased continuously from 4.8 to about 10.

The advantages of the process of the invention are apparent from the following Examples.

EXAMPLE 1

Preparation of Crude Extract

1. Bacterial cell culture.

A 12 h seed culture of *E chrysanthemi* is grown at 37° C. and added to a stirred deep culture vessel in a medium containing yeast extract and sodium glutamate to a total volume of 400 liters, essentially as described by Elsworth et al (1969). The culture is harvested by centrifugation.

2. Extraction of protein from cells.

Cell paste from 2.5 cultures are combined and suspended at a concentration of 1.5 g dry weight/100 ml of 6 mM EDTA. The suspension of 300–400 liters is stirred at 16° C. and the pH adjusted 11.3–11.5 with 0.5M NaOH. The mixture is stirred for 30 minutes and the pH is adjusted to 6.3–6.7 with 12.5% v/v acetic acid. The precipitate is removed by centrifugation and the supernatant fluid is adjusted to pH 4.8 with 25% v/v acetic acid, then centrifuged to remove the deposit.

EXAMPLE 2

Purification Using a Matrix Bearing Sulphonate Groups

Protein extracted from *E chrysanthemi* by the procedure described in Example 1 is purified as follows:

Sodium acetate buffer is prepared by the addition of 25% v/v acetic acid to 40 mM sodium acetate to pH 4.8. Sodium phosphate buffer, pH 6.0, is prepared by addition of 2M NaOH to $NaH_2PO_4$. Absorbance of protein is monitored at 280 nm and crytochrome $b_{562}$ is additionally monitored at 405 nm. The dilute extract at pH 4.8 is applied to a column of S-Sepharose Fast Flow equilibrated with 40 mM sodium acetate buffer, pH 4.8, at a linear flow rate of 300 cm/h. Unbound protein is washed from the column with equilibration buffer at the same linear flow rate. Bound protein, excluding asparaginase, but including cytochrome $b_{562}$, is eluted from the column with about 20 column volumes of 40 mM sodium phosphate, pH 6.0 6.2, at a linear flow rate of 300 cm/h.

This extensive wash is required to elute all the cytochrome $b_{562}$. L-asparaginase is eluted from the column at a linear flow rate of 100 cm/h with 40 mM sodium phosphate, pH 6.5-7.0. Successive fractions were analysed for L-asparaginase activity and the results are shown in the attached FIG. 1. Fractions containing L-asparaginase are diafiltered into 20 mM sodium phosphate, pH 6.0, the conductivity reduced to less than 1.5 mS/cm and the solution concentrated and filter sterilised.

In an alternative (and preferred) protocol, the pH was increased in a step-wise fashion and the enzyme was found to elute as a narrow peak immediately on introduction of a pH 6.8 buffer (see FIG. 2).

The results are given in the following Table 1.

TABLE 1

| Stage | Total enzyme (mega units) | Specific activity (units/mg protein) | Yield (%) |
| --- | --- | --- | --- |
| Cells (60 Kg) | 178 | 17.4 | 100 |
| Alkaline extract | 175 | 19.7 | 91 |
| Acid precipitation | 139 | 88 | 76 |
| S-Sepharose Fast Flow | 125 | 609 | 70 |
| Ultrafiltration/ concentration | 105 | 615 | 59 |

EXAMPLE 3 (COMPARATIVE)

Protein extracted from *E chrysanthemi* by the procedure described in Example 1 is purified in accordance with prior art protocols as follows:

1. Adsorption to CM-cellulose.

The supernatant fluid (conductivity <6.5 mS/cm) is diluted with demineralised water to a conductivity of about 2.5 mS/cm and stirred at 14° C. until all enzyme is adsorbed to 15 Kg CM-cellulose, previously equilibrated with 40 mM sodium acetate buffer, pH 4.8. Fluid is removed from the suspension by continuous flow centrifugation. The CM-cellulose is washed in the centrifuge with demineralised water and the excess water removed by centrifugation. The cellulose is transferred to a plastic container and the enzyme eluted from the CM-cellulose with 18 liters 40 mM NaOH containing 1 mM EDTA, pH 10.3. The CM-cellulose slurry is applied to a smaller continuous flow centrifuge and the eluate collected and retained. The CM-cellulose is recovered, added to 18 liters of elution buffer and the pH readjusted to 10.3 with 2M NaOH. The slurry is replaced in the centrifuge and the eluate collected and combined with the first eluate.

2. Acid precipitation and concentration.

The pH of the combined eluates is adjusted to 6.0 with 20% v/v orthophosphoric acid and the pH is checked after a further 45 minutes. The solution is passed through a continuous flow centrifuge, diluted to 80 liters, then concentrated to 30 liters. 45-85 liters of demineralised water is added to reduce the conductivity to below 1 mS/cm and the solution is concentrated to 3 liters. The concentration system is flushed with 7 liters of demineralised water. The concentrate is passed through a 0.5 um filtration membrane and the filtration system is flushed with 2 liters of filtered demineralised water. The solution is concentrated to 2 liters on a smaller system. If the conductivity is greater than 1.3 mS/cm demineralised water is added and the solution is again concentrated to 2 liters. The concentrator system is flushed with up to 1.5 liters of demineralised water. The pH of the solution is adjusted to 6.0 with 20% v/v orthophosphoric acid and if necessary is diluted to reduce the conductivity to below 1.3 mS. Deposit is removed from the solution by centrifugation. The solution is sterile filtered and toluene added at 1 ml/liter.

The above part of the process is repeated to provide sufficient enzyme (about 600 mega units) for the remainder of the process which is carried out under aseptic conditions. All remaining steps are carried out at 3°-6° C. unless otherwise indicated.

3. Chromatography on CM-cellulose.

Unused CM 52-cellulose is treated with 60% v/v aqueous ethanol, extensively washed with filtered demineralised water and equilibrated against sodium phosphate buffer, pH 6.0. The cellulose is packed into a 25.2×60 cm column, washed with at least one bed volume of cooled equilibration buffer, and the extract of 18 liters applied to the column at a flow rate of approximately 4 liter/hour. The column is washed with at least one bed volume of the buffer. The enzyme is eluted from the column with 60 mM sodium phosphate buffer, pH 6.0, and the active fractions collected, filtered through a 0.2 um filter membrane and combined. The combined protein solution is concentrated to 40-60 mg/ml using a hollow fibre system and then adjusted to pH 8.5 with 1M sodium hydroxide.

The results are given in the following Table 2.

TABLE 2

| Stage | Total enzyme (mega units) | Specific activity (units/mg protein) | Yield (%) |
| --- | --- | --- | --- |
| Cells (60 Kg) | 265 | 16.4 | 100 |
| Alkaline extract | 222 | 19.8 | 84 |
| Acid precipitation | 197 | 104 | 74 |
| CM-cellulose adsorption | 146 | 166 | 55 |
| Acid precipitation | 141 | 174 | 53 |
| Ultrafiltration/ concentration | 119 | 208 | 45 |
| Combined extracts | 698 | 240 | 44 |
| CM-cellulose chromatography | 635 | 620 | 40 |

EXAMPLE 4

Finishing Steps

Enzyme purified in the manner described in either of Examples 2 and 3 may be subjected to the following finishing steps:

1. Precipitation with ammonium sulphate.

Ammonium sulphate is added to the protein solution to a final concentration of 40% w/v and the suspension stirred for 1-3 h at 18°-25° C. The precipitate is recovered by centrifugation (5986 g, 30 min), dissolved in sterile distilled water and diafiltered against sterile distilled water using a hollow fibre system until the conductivity of the solution is in the range of 0.9 to 1.15 mS/cm. The solution is concentrated so the enzyme activity is in the range 65,000 to 85,000 U/ml. The pH is adjusted to 8.7 with 1M sodium hydroxide and the conductivity to between 1.2 and 1.6 mS/cm with 0.25M sodium borate buffer pH 8.7.

2. Passage through CM-cellulose.

CM 52-cellulose is treated with 60% v/v aqueous ethanol, then equilibrated with 20 mM sodium borate buffer, pH 8.7, and packed into a 25.2×45 cm column. The enzyme is applied to the column at a flow rate of approximately 5 liters/hour. The enzyme does not bind, but passes through the column. The active fractions are filtered and combined.

3. Passage through DEAE-cellulose.

DEAE 52 cellulose is equilibrated with sodium borate buffer, pH 8.7, and packed into a 25.2×60 cm column. The enzyme solution is applied to the column at a flow rate of approximately 6 liters/hour and fractions collected, filtered and combined.

4. Crystallisation.

The concentration of the enzyme solution is adjusted to between 25,000 and 35,000 U/ml by dilution with 20 mM sodium borate buffer, pH 8.7, and 0.66 volumes of ethanol is added. The solution is adjusted to pH 8.5 with 1M acetic acid and the suspension stirred for a further 1 hour at 18°–25° C. The precipitate is removed by centrifugation (5968 g for 45 mins), and 0.09 volumes ethanol is added. The solution is stored at −2° C. for 24 h before the crystals are resuspended, a further 0.1 volumes of ethanol added and the solution returned to −2° C. for at least 48 h. The supernatant fluid is decanted from the crystals, and the crystals are centrifuged (5986 g for 20 min). The sedimented crystals are dissolved in a minimum volume of sterile distilled water, and dialysed extensively against sterile distilled water at 2°–4° C. The combined dialysed enzyme solution is then made 10 mM with respect to sodium chloride and the resultant bulk enzyme solution frozen at −20° C. to await final processing.

5. Preparation of vials.

A sufficient amount of bulk enzyme solution is thawed and combined to provide material for a batch of 10,000 vials filled to 1 ml. The protein concentration is adjusted to 30 to 50 mg/ml with sterile distilled water, separated into conveniently sized batches, adjusted to pH 6.0 with 1.0M acetic acid and treated at 18°–25° C. with 0.5 volumes Alhydrogel. After stirring for 30 mins. the solutions are centrifuged (5986 g for 45 min) to remove the aluminum oxide and the supernatant fluids combined. The solution is adjusted to pH 7.4 with 1.0M sodium hydroxide and diluted to 14,000 U/ml with sterile distilled water. Sterile sodium chloride and glucose monohydrate are added to final concentrations of 10 mM and 0.5% w/v respectively. The solution is finally diluted with sterile distilled water to give an enzyme activity of 10.500 U/ml and filtered through a 0.2 um positively charged membrane filter into a sterile collection vessel. The sterile bulk product is filled into 3 ml glass vials, freeze dried and capped and crimpled under 0.5 atmosphere nitrogen.

The results are shown in the following Table 4.

TABLE 4

| Stage | Total enzyme (mega units) | Specific activity (units/mg protein) | Yield (%) |
| --- | --- | --- | --- |
| Ammonium sulphate precipitation | 558 | 650 | (100) |
| CM-cellulose passage | 530 | 700 | 95.7 |
| DE-cellulose passage | 524 | 723 | 94.2 |
| crystallization | 468 | 700 | 84.2 |
| Bulk enzyme | 433 | 700 | 77.1 |
| Depyrogenation | 411 | 700 | 72.8 |

It can be seen from Table 1 (Example 2) that the process of the invention achieved a degree of purification resulting in a specific activity >600 units/mg at a yield of 60–70% after only three purification steps (alkaline extract, acid precipitation, adsorption/elution).

On the other hand (see Table 2—Comparative Example 3) an equivalent degree of purification (specific activity >600 units/mg is achieved only after six purification steps (alkaline extract, acid precipitation, CM-cellulose adsorption, acid precipitation, ultrafiltration/concentration, CM-cellulose adsorption). Also in the prior art procedure, in reaching the aforementioned specific activity, the yield had dropped to 40%.

---

I claim:

1. A process for producing purified asparaginase which comprises the steps of
   (i) extracting L-asparaginase from disrupted cells at a pH of from 11.3 to 11.5,
   (ii) adjusting the pH to within the range 6.3 to 6.7,
   (iii) separating supernatant from precipitated impurities,
   (iv) subjecting supernatant from step (iii) to adsorption on a solid medium, having cation exchange groups so as to adsorb L-asparaginase on the solid medium wherein the cation exchange groups comprise sulphonate groups, and
   (v) eluting adsorbed L-asparaginase,
and wherein the contacting of the supernatant with the solid medium in step (iv) is effected at a pH of from 4.0 to 5.5, and wherein the eluting of adsorbed L-asparaginase in step (v) is effected at a pH of from 6.0 to 7.5.

2. A process according to claim 1 wherein the sulphonate groups form part of groups of the formula —$(CH_2)_n SO_3^-$ wherein n=1 to 3.

3. A process according to claim 1 wherein the support is derived from agarose.

4. A process according to claim 1 wherein the pH in step (v) is within the range 6.6 to 7.0.

5. A process according to claim 1 wherein the L-asparaginase subjected to purification has substantially the amino acid sequence of *E chrysanthemi* L-asparaginase.

6. A process according to claim 1 wherein the L-asparaginase subjected to purification has at least 90% sequence homology with that amino acid sequence depicted in FIG. 1.

7. A process according to claim 1 wherein the L-asparaginase subjected to purification has at least 95% sequence homology with that amino acid sequence depicted in FIG. 1.

8. A process according to claim 1 wherein the L-asparaginase subjected to purification has at least 99% sequence homology with that amino acid sequence depicted in FIG. 1.

9. A process according to claim 1 wherein the crude extract is produced by culturing a transformed microorganism containing a recombinant plasmid having a DNA insert coding for said L-asparaginase.

10. A process according to claim 1 wherein the crude extract is obtained by culturing *E chrysanthemi*.

* * * * *